United States Patent
Giorgetti (12)

(10) Patent No.: US 6,291,527 B1
(45) Date of Patent: Sep. 18, 2001

(54) PHARMACEUTICAL PREPARATIONS CONTAINING HYDROSOLUBLE KETOPROFEN SALTS AND THEIR APPLICATION

(75) Inventor: Paolo Luca Maria Giorgetti, Milan (IT)

(73) Assignee: Errekappa Euroterapici S.p.A., Milan (IT)

( * ) Notice: Subject to any disclaimer, the term of this patent is extended or adjusted under 35 U.S.C. 154(b) by 0 days.

(21) Appl. No.: 09/445,672

(22) PCT Filed: Apr. 9, 1999

(86) PCT No.: PCT/IB99/00626

§ 371 Date: Dec. 10, 1999

§ 102(e) Date: Dec. 10, 1999

(87) PCT Pub. No.: WO99/52528

PCT Pub. Date: Oct. 21, 1999

(30) Foreign Application Priority Data

Apr. 11, 1998 (CH) .................................................. 0843/98
Mar. 31, 1999 (CH) .................................................. 0618/99

(51) Int. Cl.[7] .................................................. A61K 31/19
(52) U.S. Cl. ............................................................. 514/570
(58) Field of Search ............................................. 514/570

(56) References Cited

U.S. PATENT DOCUMENTS 4,748,174    5/1988    Veronesi .

FOREIGN PATENT DOCUMENTS

| 0 523 153 | 1/1993 | (EP) . |
|---|---|---|
| 63-93718 | 4/1988 | (JP) . |
| WO 94/12451 | 6/1994 | (WO) . |
| 95 07079A | 3/1995 | (WO) . |
| 95/07103 | 3/1995 | (WO) . |
| 96/16016 | 6/1996 | (WO) . |

OTHER PUBLICATIONS

Netter, Patrick, et al., "Total and free ketoprofen in serum and synovial fluid after intramuscular injection," Clin Pharmacol Ther, vol. 42, No. 5, pp. 555–561, 1987.

Ballerini, R., et al., "Study on the Absorption of Ketoprofen Topically Administered in Man: Comparison Between Tissue and Plasma Levels," Int. J. Clin Pharms. Res. VI(1), pp. 69–72, 1986.

Köhler, G., et al., "Teneur En Principe Actif Du Sang, Du Liquide Synovial, De La Membrane Synoviale Et Des Tissus Osseux, Musculaires Et Adipeux Avoisinants Chez Dez Malades Atteints De Polyarthrite Rhumatoïde Et Ayant Reçu Une Injection Intramusculaire Unique De Kétoprofène Ou D'Acide Acetylsalicylique (Trois Heures Après Injection," Sem. Hop. Paris, vol. 48, pp. 3210–3213, 1983.

Kennedy, A.C., "Pharmacocinétique Du Kétoprofène Dans Le Liquide Synovial," Sem. Hop. Par., vol. 48, pp. 3206 & 3209, 1983.

*Primary Examiner*—William R. A. Jarvis
(74) *Attorney, Agent, or Firm*—Ladas & Parry

(57) ABSTRACT

The new pharmaceutical preparations contain hydrosoluble salts obtained through a reaction between Ketoprofen and Glucosamine and/or Proline and/or Hydroxyproline from 0.01 to 30% of the mass. Such preparations are useful for anti-inflammatory and analgesic treatment of joints and mucous membranes.

43 Claims, No Drawings

PHARMACEUTICAL PREPARATIONS CONTAINING HYDROSOLUBLE KETOPROFEN SALTS AND THEIR APPLICATION

This application is of PCT/IB 99/00626, filed Apr. 9, 1999.

This invention refers to the use of soluble Ketoprofen salts with amino acids for administration through the injectable, transdermal/mucosal and oral routes. These new compounds in addition to increasing the solubility of the active substance, are also able to increase the speed of absorption and the tolerability of the anti-inflammatory drug, as well as increasing the capacity to localize themselves in the inflammed sites in a preferential manner, particularly in inflammed joints and cartilaginous structures.

Ketoprofen is one of the most active non-steroidal anti-inflammatory drugs and, within its class of products (propionic acid derivatives), is the one with the most rapid anti-inflammatory and analgesic activity. Ketoprofen's anti-inflammatory action is exerted through various mechanisms:

a) inhibition of prostaglandin synthesis;
b) counteraction of pro-inflammatory peptide activity (e.g. bradykinin);
c) stabilization of cellular and liposomial membranes;
d) platelet anti-aggregating activity;

Ketoprofen is indicated for the treatment of rheumatoid arthritis, ankylosing spondylitis, acute gout, osteoarthrosis in various locations, sciatic pain, radiculitis, myalgia, bursitis, tendonitis, tendosynovitis, synovitis, capsulitis, very severe bruises, sprains, dislocations, muscular dilaceration, phlebitis, superficial thrombophlebitis, lymphangitis, painful inflammatory dental, ENT, and urinary tract affections and in pneumology. Injectable Ketoprofen (i.m. and i.v.) is especially indicated for the symptomatic treatment of acute pain due to inflammation of the muscular-skeletal apparatus. Topical Ketoprofen is indicated for the treatment of myalgia, muscular dilacerations, bruises, sprains, dislocations, muscular dilaceration, phlebitis, superficial thrombophlebitis, lymhangitis.

The pharmacological tests performed with Ketoprofen have demonstrated the substance's excellent tolerability and lack of acute and chronic toxicity following local application. In fact, dermal application of high quantities over extended intact and abraded surface areas in experimental animals did not induce any local or general harm, even after long term treatment. Ketoprofen, vehicled in suitable excipients and applied to the skin, is absorbed gradually. It has a half-life of 1.6 to 1.9 hours. Peak concentration following intramuscular administration is reached within 30 min.; peak mean value is 10.4 mcg/ml.

Ketoprofen's pharmacokinetic behaviour in synovial fluid is particularly interesting; and in view of the fact that this subject is the strategic part of this patent it, therefore, requires brief mention. In medical practice it has been noted that there is a limited correlation between clinical response of patients treated with anti-inflammatories and the dose administered, as well as the consequent plasma levels. This phenomenon can be correlated with the fact that the plasma concentrations are not a suitable measure of drug concentration in the joints, which are the site of the inflammatory reaction.

It is, therefore, useful to evaluate the active substance concentration in synovial fluid after oral, transdermal or intramuscular administration of a NSAID. Netter et al. (Netter P. et all., *Clin. Pharmacol. Ther.*, 42: 555–561, 7987) investigated Ketoprofen levels in plasma and synovial fluid in 37 patients (23 males and 14 females) by taking samples at various intervals between 15 minutes and 15 hours after intramuscular administration of 100 mg.

The results obtained demonstrate that Ketoprofen penetrates promptly into the joints, in view of the significant concentrations that are detectable even 15 minutes after administration.

The maximum serum concentration is reached after 30 minutes (6.5 μg/ml); whilst equilibrium, i.e.: when serum and synovial concentrations are equivalent, is reached after 3.5 hours (1.3 μg/ml). After 8 to 15 hours from intramuscular administration of 100 mg Ketoprofen concentrations in synovial fluid are treble those observable in serum. The AUC of the free Ketoprofen fraction in serum is 127 hr*ng*ml$^{-1}$, whilst in synovial fluid it is 119 hr*ng*ml$^{-1}$. Mean resident time in the joints was about three times longer than that observed in serum.

Ballerini et al. (Ballerini R. et all., *Int. J. Clin. Pharm. Res VI*: 69–72, 1986) also investigated the concentrations of Ketoprofen in the joints and in circulation. They administered a Ketoprofen gel to 6 patients who were to undergo a knee operation and in whom it was possible to determine the presence of the active substance in the intraarticular adipose tissue, in the capsular tissue and in synovial fluid. The gel was applied once a day for three days; the operations were performed 12 hours after the last administration. Ketoprofen was detectable from the 2nd hour (6.3 ng/ml) and reached peak concentration after six hours (18.2 ng/l) with values that remained constant for 12 hours. In synovial fluid mean values after 12 hours were 1.31 mcg/g, whilst in intraarticular adipose tissue they were 4.70 mcg/g and in the capsular tissue 2.36 mcg/g. The data obtained show a greater active substance concentration in the joint than in systemic circulation indicating a direct transdermal diffusion in the joint without direct involvement of circulatory flow, in which the active principle is present only due to local diffusion.

Kohler et al. (Kohler G. et all., *Sem. Hop. Par.*, 48: 3210–3213, 1983) investigated 16 patients affected by rheumatoid polyarthritis or deforming arthrosis subjected to surgical procedures. The patients were treated with Ketoprofen 100 mg administered i.m. approximately 3 hours before the operation.

The mean values observed were 0.85 μg/g in synovial fluid, 0.32 μg/g in the synovial membrane, 0.25 μg/g in bone, 0.26 μg/g in muscle, 0.28 μg/g in fat, and 1.39 μg/g in blood.

Finally Kennedy (Kennedy A.C. *Sem. Hop. Par.*, 48: 3206–3209, 1983) investigated Ketoprofen levels in the synovial fluid of patients affected by rheumatoid arthritis, by treating 6 subjects with 100 mg and 5 subjects with 50 mg, administered orally. The resulting concentrations demonstrated that in synovial fluid, after administration of Ketoprofen 50 mg, the peak (0.91 μg/ml) appears approximately two hours after the plasma peak; whilst with a 100 mg dose synovial concentrations remained practically stable for a period of 3 to 6 hours after treatment.

It is, therefore, possible to conclude that, following treatment through various routes of administration, the intraarticular Ketoprofen concentrations reach peak levels later with respect to those observable in serum and plasma, but remain at higher levels than the latter for a longer period after treatment and always with higher values compared to those present in circulatory flow.

Ketoprofen is mainly excreted with urine (>50% in the form of metabolites) and only a minimal percentage is eliminated with the feces (1%).

Toxicity studies have demonstrated Ketoprofen's low toxicity and high therapeutical ratio. The oral $LD_{50}$ in the rat is 165 mg/kg; whilst in the mouse, for various routes of administration, it is between 365 and 662 mg/kg.

Ketoprofen, 3-Benzoyl-α-methylbenzeneacetic acid, $C_{16}H_{14}O_3$; mol wt 254,29 is practically insoluble in water, in acid solutions, and soluble in alkaline solutions. This substance's solubility in water can be modified when the molecule is salified with inorganic or organic bases.

The use of Ketoprofen salts has always attracted substantial interest because of the evident improvements obtainable with regard to bioavailability, tolerability and compliance (use of more suitable and specific pharmaceutical presentations).

Numerous developments and patents have been obtained in this field; for example it is possible to mention the use of K sodium salt, Arginine, Lysine and Methylglucamine salt for use in soft gelatin capsules(PCT/FR91/00273).

Another patent (PCT/US94/09581) describes the composition of anti-inflammatories such as Ibuprofen, Naproxen, Ketoprofen, among which Lysine, Choline Arginine, Glucosamine salts.

Particular interest is directed towards the following three amino acids which, thanks to their basicity, solubility and pharmacological properties, can form interesting Ketoprofen salts: Glucosamine, Proline and Hydroxyproline.

Glucosamine, 2-Amino-2-deoxy-D-glucose, $C_6H_{13}NO_5$, mol wt 35 179.17, an amino sugar that occurs naturally in the human body, is used for the biosynthesis of hyaluronic acid in synovial fluid and proteoglycans of the interstitial substance of joint cartilage.

Glucosamine is normally synthesized starting from glucose. During arthrosis there is a metabolic deficit in the biosynthesis of Glucosamines and proteoglycans. In this condition exogenous supply of Glucosamine compensates the substance's endogenous deficit, it stimulates biosynthesis of proteoglycans, exerts a trophic action on articular cartilage and favours fixation of sulphur for the synthesis of chondroitinsulfuric acid. All these activites have a favourable effect on cartilage degenerative processes that are at the basis of arthrosis.

Proline (l-Proline, $C_5H_9N_2$, mol wt 115.13) and Hydroxyproline (trans-4-Hydroxyproline, $C_5H_9NO_3$ mol wt 131.13) are two special amino acids since they do not possess an aminic group (—$NH_2$), but an iminic group (—NH—). Their presence in special polypeptide chain sites allows proteins certain curves which have structural importance. Hydroxyproline is not present in the majority of proteins and is typical of connectival proteins (collagen, elastin); it is contained in collagen as an essential component at a ratio of 10%. Ketoprofen Glucosamine, Proline and Hydroxyproline salts have been investigated following injectable, topical and oral administration for the assessment of their anti-inflammatory activity.

There are two methods of preparation for Ketoprofen Glucosamine, Proline and Hydroxyproline salts
  a) extemporaneous preparation in aqueous solvent
  b) preparation using organic solvent The first method appears to be the most logical when one wishes to obtain a salt; in such case, the solution can be used promptly for the preparation of water-based formulations (injectable preparations, water emulsions, oral solutions, etc.).

The second method is used for the preparation of the salt in order to achieve a solid substance for use in solid preparations such as, for example, tablets, granules, suppositories, etc.

Preparation of Ketoprofen Glucosamine salt through the aqueous route is carried out with stoichiometric quantities at the ratio of 1:1 of Ketoprofen and Glucosamine base, according to the following procedure:

1# Weigh 179.17 g of Glucosamine base and dissolve in 300 ml of purified water.
2# After complete dissolution, add and dissolve under stirring 254.29 g of Ketoprofen acid.
3# To aid dissolution, thermostat to 35–40° C., control the pH which must be neutralized by adjustment, if required, adding either Ketoprofen (if the pH is basic) or Glucosamine base (if the pH is acid).
4# Cool to room temperature and bring to 1 litre volume with water.
5# Filter through a sterilizing membrane with 0.22 micron porosity. A Ketoprofen Glucosamine salt solution has thus been obtained having a concentration of 433.4 g/litre.

Preparation of Ketoprofen Proline salt through the aqueous route is carried out with stoichiometric quantities at the ratio of 1:1 of Ketoprofen and Proline base, according to the following procedure:

1# Weigh 115.13 g of Proline base and dissolve in 300 ml of purified water.
2# After complete dissolution, add and dissolve under stirring 254.29 g of Ketoprofen acid.
3# To aid dissolution, thermostat to 35–40° C., control the pH which must be neutralized by adjustment, if required, adding either Ketoprofen (if the pH is basic) or Proline base (if the pH is acid).
4# Cool to room temperature and bring to 1 litre volume with water.
5# Filter through a sterilizing membrane with 0.22 micron porosity. A Ketoprofen Proline salt solution has thus been obtained having a concentration of 369.42 g/litre.

Preparation of Ketoprofen Hydroxyproline base through the aqueous route is carried out with stoichiometric quantities at the ratio of 1:1 of Ketoprofen and Hydroxyproline base, according to the following procedure:

1# Weigh 131.13 g of Hydroxyproline base and dissolve in 300 ml of purified water.
2# After complete dissolution, add and dissolve under stirring 254.29 g Ketoprofen acid.
3# To aid dissolution, thermostat to 35–40° C., control the pH which must be neutralized by adjustment, if required, adding either Ketoprofen (if the pH is basic) or Hydroxyproline base (if the pH is acid).
4# Cool to room temperature and bring to 1 litre volume with water.
5# Filter through a sterilizing membrane with 0.22 micron porosity. A Ketoprofen Hydroxyproline salt solution has thus been obtained having a concentration of 385.42 g/liter.

Preparation with organic solvent involves dissolution of Ketoprofen in organic solvent (for example pure ethanol) and salification by adding and dissolving Glucosamine, or Proline, or liydroxyproline, according to the above mentioned stoichiometric ratios.

This is followed by filtration through a porous sintered glass septum, then elimination of the organic solvent using a rotating vacuum evaporator. The residue obtained is dried in a vacuum oven, then reduced and dimensioned to powder.

The three above mentioned Ketoprofen salts were compared with Ketoprofen acid and Ketoprofen sodium salt in animal studies.

Investigation in experimental animals evidenced a surprising increase in anti-inflammatory and analgesic activity.

In particular:
a) Injection of Ketoprofen Glucosamine salts produced a high active substance concentration in the inflammed site, which was much greater than that observed with Ketoprofen sodium salt. The Proline and Hydroxyproline salts reach intermediate concentrations between the sodium salt and the Glucosamine salt.
b) Ketoprofen Glucosamine, Proline and Hydroxyproline salts administered orally indicated kinetic parameters that were significantly different with respect to Ketoprofen acid and Ketoprofen sodium salt.
c) In the above mentioned tests, Ketoprofen Glucosamine salt shows a surprising affinity for cartilage and connective tissue enabling targetted vehicolation to the inflammatory sites.

The pharmacological and pharmacodynamic properties of Ketoprofen Glucosamine, Proline and Hydroxyproline salts enable the preparation of formulations for rational pharmaceutical presentantions that lead to an improvement in drug activity, thus increasing compliance.

This invention is characterized by the claims that follow and may be described in a more detailed manner with the aid of formulation examples that are not to be considered as a limit for the invention.

Furthermore, the anti-inflammatory activity of Ketoprofen Glucosamine salt and Ketoprofen Lysine salt, compared to that of Ketoprofen, has been assessed in the rat using the carrageen edema model and the foreign body (sponge) method.

The carrageen edema tests in the rat were carried out on 80 male animals of the Wistar (Charles River, Calco, LC, Italy) strain weighing 160±5 g.

The Winter et al. method was used which enables assessment of drug activity in the acute phase of the inflammatory process that is essentially related to increased vascular (edema) permeability and substantial infiltration of polymorphonucleated granulocytes in the exudate.

In particular, 100 µl of carrageen at a 1% concentration dissolved in sterile physiological solution, were injected into the hind paw aponeurosis of animals that had been fasted (water ad libitum)from the evening prior to the experiment.

In order to obtain greater uniformity in the development of the edema, the animals were treated orally with 5 ml of physiological solution 2 hours before the test.

Evolution of edema induced by administration of carrageen was assessed with the plethysmographic method using a device (plethysmometer, mod. 7150) manufactured by U. Basile, Comerio, Varese, Italy.

Measurement of paw volume was carried out immediately after injection of the phlogogenic agent (T0) and at each hour up to the 6th hour following treatment. The animals, randomly divided into 8 experimental groups (10 per group), were treated orally (using a gastric probe) with Ketoprofen Glucosamine salt, Ketoprofen Lysine salt and with Ketoprofen, 30 minutes before carrageen, according to the following experimental protocol:

| Controls (physiologial solution, 1 ml/kg) | 10 animals |
| Ketoprofen Glucosamine salt (0.5 mg/kg) | 10 animals |
| Ketoprofen Glucosamine salt (1 mg/kg) | 10 animals |
| Ketoprofen Glucosamine salt (2 mg/kg) | 10 animals |
| Ketoprofen Lysine salt (0.5 mg/kg) | 10 animals |
| Ketoprofen Lysine salt (1 mg/kg) | 10 animals |
| Ketoprofen Lysine salt (2 mg/kg) | 10 animals |
| Ketoprofen (10 mg/kg) | 10 animals |

Since Ketoprofen's anti-inflammatory activity, as that of all propionic acid derivatives, is largely due to inhibition of the cyclooxygenase enzyme and, therefore, blockade of arachidonic acid oxidative cascade, the experimental "sponge" model in the rat described by Higgs et al. is particularly suitable for the evaluation of the vascular exudation phenomenon and related new formation of primary prostaglandin.

These tests involved the use of 100 male CD strain rats (Charles River, Calco, LC, Italy) weighing 180±8 g. The animals were fasted for 12 hours (water ad libitum) before being used for the experiment.

The inflammatory reaction with the formation of exudate was induced by using sterilized polyester sponges (4×1.5× 0.5 cm) soaked in carrageen dissolved at a 2% concentration in sterile physiological solution. The rats were anesthetized lightly with ether and two sponges per rat were implanted subcutaneously in a previously shaven dorsal area. The animals, randomly divided into 10 experimental groups (10 per group), were treated orally (using a gastric probe) with Ketoprofen Glucosamine salt, Ketoprofen Lysine salt and Ketoprofen, immediately after implantation of the sponges (T0) according to the following experimental protocol:

| Controls (physiologial solution, 1 ml/kg) | 10 animals |
| Ketoprofen Glucosamine salt (0.5 mg/kg) | 10 animals |
| Ketoprofen Glucosamine salt (1 mg/kg) | 10 animals |
| Ketoprofen Glucosamine salt (2 mg/kg) | 10 animals |
| Ketoprofen Glucosamine salt (4 mg/kg) | 10 animals |
| Ketoprofen Lysine salt (0.5 mg/kg) | 10 animals |
| Ketoprofen Lysine salt (1 mg/kg) | 10 animals |
| Ketoprofen Lysine salt (2 mg/kg) | 10 animals |
| Ketoprofen Lysine salt (4 mg/kg) | 10 animals |
| Ketoprofen (10 mg/kg) | 10 animals |

The sponges were removed 8 hours later after having sacrificed the animals by ether euthanasia, and immediately placed in large polyethylene 50 ml test tubes containing 10 ml of heparinized physiological solution. The test tubes were then subjected to centrifugation (1000 rotations; 15 minutes), followed by removal of the sponges and accurate measurement of the volume of the remaining fluid. Always using the Higgs et al. method, the acid lipids present in the fluid were extracted in chloroform with prior dilution in ethanol and acidification to pH 3. After complete evaporation of the chloroform, the remaining dry residue was dissolved in physiological solution and used for the immunoenzymatic assay of prostaglandin $E_2$ ($PGE_2$).

The following substances and experimental materials were used for these tests: Ketoprofen Glucosamine salt and ketoprofen Lysine salt, Ketoprofen and type IV carrageen (Sigma-Aldrich, Milan, Italy); a kit for the immunoenzymatic assay of $PGE_2$ (Amersham, Milan, Italy). All the other reagents used for the tests were purchased from Merck-Bracco (Milan, Italy).

The data obtained during these tests were processed with the variance analysis (ANOVA) and Student's "t" test for independent data, considering significant the differences with $p<0.05$. Multiple comparisons between the various experimental groups were carried out using the statistical Tukey-Kramer test. The area underneath the curve (AUC) was calculated with the trapezoid method using a computer programme (Microcal Origin, version 3.5).

The results obtained for the carrageen edema test in the rat indicate that Ketoprofen Glucosamine salt, administered orally at doses of 0.5, 1 and 2 mg/kg, possesses anti-inflammatory activity. The anti-edematogenic effect of the test compound is dose-dependent. In fact, considering the values obtained by measuring the area underneath the curve (AUC), Ketoprofen Glucosamine salt significantly inhibits (p<0.001) the reaction process by 30%, 48% and 72% at the oral doses of 0.5, 1 and 2 mg/kg respectively (Tables 1–2).

The anti-inflammatory activity observed with Ketoprofen Glucosamine salt is comparable with that obtained by administering Ketoprofen Lysine salt to rats at the oral doses of 0.5, 1 and 2 mg/kg. In fact, the $ED_{50}$ values of the two compounds (extrapolated from the data obtained with the AUC) resulted equal to 1.104 mg/kg per os (95% confidence limit: 0.733–1.474) and 1.383 mg/kg per os (95% confidence limit: 1.198–1.567) respectively for Ketoprofen Glucosamine salt and Ketoprofen Lysine salt (Table 2).

In this test Ketoprofen (used as internal positive standard) also resulted as having anti-inflammatory activity. In fact, this substance administered to rats at the dose of 10 mg/kg per os, inhibits (54.1%; p<0.001) the inflammatory reaction caused by injection of carrageen in the paw aponeurosis (Tables 1–2).

The results obtained in the test with induction of edema using foreign body implantation (sponge) in the rat and reported in Table 3, clearly indicate that Ketoprofen Glucosamine salt controls the vasculo-exudative inflammatory response in a dose dependent manner (0.5, 1, 2 and 4 mg/kg per os). In fact, Ketoprofen Glucosamine salt is able to significantly counteract the evolution of the reaction above all in terms of minor formation of inflammatory exudate correlated with singificant inhibition of PGE2 activity in such exudates (Table 3).

Ketoprofen Lysine salt administered to animals at a dose of 0.5, 1, 2 and 4 mg/kg per os, also demonstrated that it is able to control the inflammatory response of the host of the subcutaneous foreign body implant (Table 3).

TABLE 1

Table 1 illustrates the anti-inflammatory activity of Ketoprofen Glucosamine salt (KGS), Ketoprofen Lysine salt (KLS) and Ketoprofen (KETO) in the rat: carrageen edema test. The data represent the mean ± MSE of 10 rats per group. The compounds were administered orally 60 min before the inflammatory agent (carrageen 1%). Baseline paw volume was 1.70 ± 0.02 ml (n = 80).

| COMPOUND | EVOLUTION OF PAW VOLUME (delta in ml) at: | | | | | |
|---|---|---|---|---|---|---|
| mg/kg/os | 1st hour | 2nd hour | 3rd hour | 4th hour | 5th hour | 6th hour |
| CONTROLS | 0.40 ± 0.02 | 0.71 ± 0.02 | 0.87 ± 0.03 | 0.93 ± 0.03 | 0.90 ± 0.04 | 0.84 ± 0.04 |
| KGS 0.5 | 0.28 ± 0.02 | 0.51 ± 0.03 | 0.62 ± 0.04 | 0.65 ± 0.04 | 0.62 ± 0.05 | 0.56 ± 0.05 |
| KGS 1 | 0.23 ± 0.01 | 0.39 ± 0.02 | 0.46 ± 0.02 | 0.48 ± 0.02 | 0.45 ± 0.02 | 0.39 ± 0.03 |
| KGS 2 | 0.11 ± 0.02 | 0.20 ± 0.02 | 0.26 ± 0.03 | 0.28 ± 0.03 | 0.25 ± 0.03 | 0.16 ± 0.02 |
| KLS 0.5 | 0.32 ± 0.02 | 0.53 ± 0.03 | 0.66 ± 0.04 | 0.70 ± 0.03 | 0.68 ± 0.02 | 0.64 ± 0.03 |
| KLS 1 | 0.24 ± 0.02 | 0.43 ± 0.03 | 0.54 ± 0.03 | 0.59 ± 0.03 | 0.57 ± 0.03 | 0.49 ± 0.03 |
| KLS 2 | 0.13 ± 0.02 | 0.23 ± 0.02 | 0.28 ± 0.02 | 0.29 ± 0.02 | 0.28 ± 0.02 | 0.23 ± 0.03 |
| KETO 10 | 0.19 ± 0.02 | 0.33 ± 0.03 | 0.41 ± 0.02 | 0.42 ± 0.02 | 0.40 ± 0.03 | 0.37 ± 0.03 |

TABLE 2

Table 2 illustrates the areas underneath the curve (AUC) related to evolution through time of the increases in paw volume.
The compounds were administered orally 60 min before carrageen. The AUC were calculated with the trapezoid method [in ordinates: paw volume (delta in ml); in abscissa: time (from 0 to 6 hours)]. All the differences versus controls were highly significant (p < 0.001) (ANOVA + Tukey-Kramer test).

| SUBSTANCE | ORAL DOSE mg/kg | No. rats | AUC (mean ± MSE) | % inhibition vs controls | ORAL $ED_{50}$ mg/kg (95% conf. Lim.) |
|---|---|---|---|---|---|
| CONTROLS | — | 10 | 4.23 ± 0.26 | — | — |
| KGS | 0.5 | 10 | 2.96 ± 0.15 | 30.0 | 1.104 |
| KGS | 1 | 10 | 2.20 ± 0.13 | 48.0 | (0.733–1.474) |
| KGS | 2 | 10 | 1.18 ± 0.06 | 72.1 | |
| KLS | 0.5 | 10 | 3.21 ± 0.17 | 24.1 | 1.383 |
| KLS | 1 | 10 | 2.62 ± 0.12 | 38.0 | (1.198–1.567) |
| KLS | 2 | 10 | 1.33 ± 0.07 | 68.6 | |
| KETO | 10 | 10 | 1.94 ± 0.10 | 54.1 | — |

TABLE 3

Table 3 indicates the effect of Ketoprofen Glucosamine salt (KGS), Ketoprofen Lysine salt (KLS) and Ketoprofen (KETO) on the concentration of prostaglandin $E_2$ ($PGE_2$) present in the inflammatory exudate (IE) obtained 8 hours after subcutaneous implantation of two polyester sponges soaked in carrageen (0.5%) in rats. The compounds were administered orally immediately after implantation of the sponges. The values are expressed as mean ± MSE. The % inhibition versus controls is placed in brackets.
a: $p < 0.05$ b: $p < 0.01$; c: $p < 0.001$ (ANOVA + Tukey-Kramer test).

| SUBSTANCE | DOSE mg/kg os | No. rats | IE (ml) | $PGE_2$ (ng/ml) |
|---|---|---|---|---|
| CONTROLS | — | 10 | 5.15 ± 0.28 (—) | 98.7 ± 4.7 (—) |
| KGS | 0.5 | 10 | 3.87 ± 0.27 (24.8)b | 67.6 ± 4.1 (31.5)c |
| KGS | 1 | 10 | 3.56 ± 0.28 (30.9)c | 60.5 ± 3.0 (38.7)c |
| KGS | 2 | 10 | 2.53 ± 0.22 (50.9)c | 49.9 ± 2.1 (49.4)c |
| KGS | 4 | 10 | 1.05 ± 0.09 (79.6)c | 24.9 ± 2.3 (74.8)c |
| KLS | 0.5 | 10 | 4.33 ± 0.26 (15.9)a | 78.1 ± 3.7 (20.9)b |
| KLS | 1 | 10 | 3.82 ± 0.15 (25.8)b | 67.9 ± 3.5 (31.2)c |
| KLS | 2 | 10 | 2.97 ± 0.19 (42.3)c | 55.6 ± 2.3 (43.7)c |
| KLS | 4 | 10 | 1.68 ± 0.14 (67.4)c | 32.8 ± 1.8 (66.8)c |
| KETO | 10 | 10 | 2.13 ± 0.15 (58.6)c | 49.6 ± 3.0 (49.7)c |

TABLE 4

Table 4 contains the values of the $ED_{50}$ for Ketoprofen Glucosamine salt (KGS), Ketoprofen Lysine salt (KLS) on the concentration of prostaglandin $E_2$ ($PGE_2$) present in the inflammatory exudate (IE) obtained 8 hours after implantation of two polyester sponges soaked in carrageen (0.5%) in rats. The compounds were administered orally immediately after implantation of the sponges. The values of the Efficacy Dose ($ED_{50}$) were calculated using the data reported in table 3. The values in brackets represent the 95% confidence limits.

| SUB-STANCE | DOSE mg/kg os | IE (ml) (ORAL $ED_{50}$ mg/kg) | $PGE_2$ (ORAL $ED_{50}$ mg/kg) |
|---|---|---|---|
| KGS | 0.5 | | |
| KGS | 1 | 2.092 | 1.989 |
| KGS | 2 | (1.802–2.381) | (1.848–2.131) |
| KGS | 4 | | |
| KLS | 0.5 | | |
| KLS | 1 | 2.714 | 2.610 |
| KLS | 2 | (2.334–3.094) | (2.215–3.005) |
| KLS | 4 | | |

The invention is characterized by the nine claims that follow.

The following represent examples of pharmaceutical preparations in accordance with the invention.

EXAMPLE NO. 1

INJECTABLE PREPARATION FOR INTRAMUSCULAR ADMINISTRATION

| SUBSTANCE | QUANTITY FOR 1 UNIT |
|---|---|
| Active substance: | |
| Ketoprofen Glucosamine salt | 170 mg |
| equivalent to Ketoprofen acid | 100 mg |
| Excipients: | |
| Benzyl alcohol | 90 mg |
| Sodium chloride | 27 mg |
| Water for injectable preparations | up to: 3 ml |

EXAMPLE NO. 2

INJECTABLE PREPARATION FOR INTRAVENOUS ADMINISTRATION

| SUBSTANCE | QUANTITY FOR 1 UNIT |
|---|---|
| Active substance: | |
| Ketoprofen Glucosamine salt | 170 mg |
| equivalent to Ketoprofen acid | 100 mg |
| Excipients: | |
| Fructose | 700 mg |
| Water for injectable preparations | up to: 10 ml |

EXAMPLE NO. 3

LARGE VOLUME PREPARATION FOR INTRAVENOUS ADMINISTRATION

| SUBSTANCE | QUANTITY FOR 1 UNIT |
|---|---|
| Active substance: | |
| Ketoprofen Glucosamine salt | 170 mg |
| equivalent to Ketoprofen acid | 100 mg |
| Excipients: | |
| Anhydrous glucose | 25 g |
| Water for injectable preparations | up to: 500 ml |

EXAMPLE NO. 4

TABLETS

| SUBSTANCE | QUANTITY FOR 1 UNIT |
|---|---|
| Active substance: | |
| Ketoprofen Glucosamine salt | 170 mg |
| equivalent to Ketoprofen acid | 100 mg |

-continued

| SUBSTANCE | QUANTITY FOR 1 UNIT |
|---|---|
| Excipients: | |
| Corn starch | 100 mg |
| Pyrogenic silica | 15 mg |
| Microcrystalline cellulose | 110 mg |
| Talc | 3 mg |
| Magnesium stearate | 2 mg |

EXAMPLE NO. 5
GASTRORESISTANT TABLETS

| SUBSTANCE | QUANTITY FOR 1 UNIT |
|---|---|
| Active substance: | |
| Ketoprofen Glucosamine salt | 170 mg |
| equivalent to Ketoprofen acid | 100 mg |
| Nucleus excipients: | |
| Granular cellulose | 110 mg |
| Dried spray lactose | 100 mg |
| Talc | 5 mg |
| Glycerol beenate | 15 mg |
| Coating excipients: | |
| Cellulose acetophthalate | 10 mg |
| Diethylphthalate | 1 mg |
| Titanium dioxide | 2 mg |
| Talc | 8 mg |

EXAMPLE NO. 6
COATED TABLETS

| SUBSTANCE | QUANTITY FOR 1 UNIT |
|---|---|
| Active substance: | |
| Ketoprofen Glucosamine salt | 170 mg |
| equivalent to Ketoprofen acid | 100 mg |
| Nucleus excipients: | |
| Granular cellulose | 110 mg |
| Magnesium oxide | 100 mg |
| Talc | 5 mg |
| Glycerol beenate | 15 mg |
| Coating excipients: | |
| Methylcellulose | 10 mg |
| Triacetin | 1 mg |
| Titanium Dioxide | 1 mg |
| E172 | 1 mg |
| Talc | 2 mg |

EXAMPLE NO. 7
CAPSULAS

| SUBSTANCE | QUANTITY FOR 1 UNIT |
|---|---|
| Active substance: | |
| Ketoprofen Glucosamine salt | 85 mg |
| equivalent to Ketoprofen acid | 50 mg |

-continued

| SUBSTANCE | QUANTITY FOR 1 UNIT |
|---|---|
| Excipients: | |
| Pyrogenic silica | 5 mg |
| Levilite | 20 mg |
| Cellulose | 50 mg |
| Talc | 2 mg |
| Magnesium stearate | 3 mg |
| White non-transparent size 1 capsules | |

EXAMPLE NO. 8
GASTRORESISTANT CAPSULES

| SUBSTANCE | QUANTITY FOR 1 UNIT |
|---|---|
| Active substance: | |
| Ketoprofen Glucosamine salt | 85 mg |
| equivalent to Ketoprofen acid | 50 mg |
| Excipients: | |
| Pyrogenic silica | 5 mg |
| Levilite | 20 mg |
| Cellulose | 50 mg |
| Talc | 2 mg |
| Magnesium stearate | 3 mg |
| White non-transparent size 1 capsules | |
| Coating excipients: | |
| Methylcellulose | 10 mg |
| Triacetin | 1 mg |
| Titanium Dioxide | 2 mg |
| E172 | 2 mg |
| Talc | 5 mg |

EXAMPLE NO. 9
SOFT CAPSULES

| SUBSTANCE | QUANTITY FOR 1 UNIT |
|---|---|
| Active substance: | |
| Ketoprofen Glucosamine salt | 85 mg |
| equivalent to Ketoprofen acid | 50 mg |
| Excipients: | |
| Mineral oil | 115 mg |
| Food gelatin | 50 mg |
| Titanium dioxide | 5 mg |

EXAMPLE NO. 10
EXTEMPORANEOUS GRANULES

| SUBSTANCE | QUANTITY FOR 1 UNIT |
|---|---|
| Active substance: | |
| Ketoprofen Glucosamine salt | 85 mg |
| equivalent to Ketoprofen acid | 50 mg |

-continued

| SUBSTANCE | QUANTITY FOR 1 UNIT |
|---|---|
| Excipients: | |
| Mannitol | 315 mg |
| Maltodextrin based lyophilized orange flavouring | 3500 mg |
| Lemon flavouring | 80 mg |
| Potassium acesulfame | 20 mg |

EXAMPLE NO. 11
SLOW RELEASE TABLETS (MATRIX SYSTEM)

| SUBSTANCE | QUANTITY FOR 1 UNIT |
|---|---|
| Active substance: | |
| Ketoprofen Glucosamine salt | 170 mg |
| equivalent to Ketoprofen acid | 100 mg |
| Excipients: | |
| Methylcellulose | 50 mg |
| Ethylcellulose | 100 mg |
| Talc | 20 mg |
| Magnesium stearate | 5 mg |

EXAMPLE NO. 12
CAPSULES WITH TARGETTED RELEASE

| SUBSTANCE | QUANTITY FOR 1 UNIT |
|---|---|
| Active substance: | |
| Ketoprofen Glucosamine salt | 85 mg |
| equivalent to Ketoprofen acid | 50 mg |
| Excipients: | |
| Pyrogenic silica | 5 mg |
| Levilite | 20 mg |
| Cellulose | 50 mg |
| Talc | 2 mg |
| Magnesium stearate | 3 mg |
| White non-transparent size 1 capsules | |
| Coating excipients: | |
| Eudragit S | 20 mg |
| Eudragit L | 20 mg |
| Triacetin | 1 mg |
| Titanium dioxide | 2 mg |
| E172 | 2 mg |
| Talc | 5 mg |

EXAMPLE NO. 13
SLOW RELEASE GRANULES

| SUBSTANCE | QUANTITY FOR 1 UNIT |
|---|---|
| Active substance: | |
| Ketoprofen Glucosamine salt | 170 mg |
| equivalent to Ketoprofen acid | 100 mg |

-continued

| SUBSTANCE | QUANTITY FOR 1 UNIT |
|---|---|
| Excipients: | |
| Eudragit S | 30 mg |
| Eudragit L | 30 mg |
| Lactose | 2000 mg |
| Saccharin sodium | 20 mg |
| Wild fruits flavouring | 50 mg |

EXAMPLE NO. 14
SLOW RELEASE ORAL SUSPENSIONS

| SUBSTANCE | QUANTITY FOR 1 UNIT |
|---|---|
| Active substance: | |
| Ketoprofen Glucosamine salt | 1.7 g |
| equivalent to Ketoprofen acid | 1 g |
| Excipients: | |
| Eudragit S | 3 g |
| Eudragit L | 3 g |
| Sucrose | 20 g |
| Arabic gum | 0.5 g |
| Saccharin sodium | 0.2 g |
| Wild fruits flavouring | 0.2 g |
| Sodium benzoate | 0.1 g |
| Purified water | up to: 100 ml |

EXAMPLE NO. 15
CHEWING GUM

| SUBSTANCE | QUANTITY FOR 1 UNIT |
|---|---|
| Active substance: | |
| Ketoprofen Glucosamine salt | 85 mg |
| equivalent to Ketoprofen acid | 50 mg |
| Excipients: | |
| Gum | 2.0 g |
| Sucrose | 2.0 g |
| Orange flavouring | 0.1 g |
| Lemon flavouring | 0.1 g |
| Talc | 0.01 g |

EXAMPLE NO. 16
GINGIVAL GEL

| SUBSTANCE | QUANTITY FOR 1 UNIT |
|---|---|
| Active substance: | |
| Ketoprofen Glucosamine salt | 3.4 g |
| equivalent to Ketoprofen acid | 2 g |
| Excipients | |
| Carbopol 940 | 1.0 g |
| Sodium hyaluronate | 1.0 g |
| Methyl-p-hydroxybenzoate | 0.1 g |
| Purified water | up to: 100 g |

EXAMPLE NO. 17

MOUTHWASH SOLUTION

| SUBSTANCE | QUANTITY FOR 1 UNIT |
|---|---|
| Active substance: | |
| Ketoprofen Glucosamine salt | 1.7 g |
| equivalent to Ketoprofen acid | 1 g |
| Excipients: | |
| Ethyl alcohol 95° | 10.0 g |
| Sorbitol 70% | 30.0 g |
| Saccharin sodium | 0.1 g |
| Pluronic | 0.9 g |
| Mint flavouring | 0.1 g |
| Potassium sorbate | 0.5 g |
| Purified water | up to: 100 ml |

EXAMPLE NO. 18

SOLUTIONS FOR CANALAR TREATMENT

| SUBSTANCE | QUANTITY FOR 1 UNIT |
|---|---|
| Active substance: | |
| Ketoprofen Glucosamine salt | 17 g |
| equivalent to Ketoprofen acid | 10 g |
| Excipients: | |
| Chlorhexidine gluconate | 0.5 g |
| Purified water | up to: 100 ml |

EXAMPLE NO. 19

SUPPOSITORIES

| SUBSTANCE | QUANTITY FOR 1 UNIT |
|---|---|
| Active substance: | |
| Ketoprofen Glucosamine salt | 170 mg |
| equivalent to Ketoprofen acid | 100 mg |
| Excipients: | |
| Witepsl H 15 | up to: 4 g |

EXAMPLE NO. 20

VAGINAL BOUGIES

| SUBSTANCE | QUANTITY FOR 1 UNIT |
|---|---|
| Active substance: | |
| Ketoprofen Glucosamine salt | 85 mg |
| equivalent to Ketoprofen acid | 50 mg |
| Excipients: | |
| Supposire BS2X | up to: 3.5 g |

EXAMPLE NO. 21

SOLUTIONS FOR VAGINAL IRRIGATION

| SUBSTANCE | QUANTITY FOR 1 UNIT |
|---|---|
| Active substance: | |
| Ketoprofen Glucosamine salt | 85 mg |
| equivalent to Ketoprofen acid | 50 mg |
| Excipients: | |
| Tween 20 | 500 mg |
| Rose perfume | 100 mg |
| Propylene glycol | 1000 mg |
| Methyl-p-hydroxybenzoate | 0.100 mg |
| Propyl-p-hydroxybenzoate | 0.050 mg |
| Purified water | up to: 100 ml |

EXAMPLE NO. 22

VAGINAL CREAM WITH APPLICATOR

| SUBSTANCE | QUANTITY FOR 1 UNIT |
|---|---|
| Active substance: | |
| Ketoprofen Glucosamine salt | 17 g |
| equivalent to Ketoprofen acid | 10% |
| Excipients: | |
| Mineral oil | 10 g |
| Tefose 63 | 18 g |
| Propylene glycol | 3 g |
| Methyl-p-hydroxybenzoate | 0.1 g |
| Propyl-p-hydroxybenzoate | 0.05 g |
| Purified water | up to: 100 g |

EXAMPLE NO. 23

VAGINAL GEL WITH APPLICATOR

| SUBSTANCE | QUANTITY FOR 1 UNIT |
|---|---|
| Active substance: | |
| Ketoprofen Glucosamine salt | 17 g |
| equivalent to Ketoprofen acid | 10% |
| Excipients: | |
| Carbopol 934 | 2 g |
| Propylene glycol | 20 g |
| Methyl-p-hydroxybenzoate | 0.1 g |
| Propyl-p-hydroxybenzoate | 0.05 g |
| Purified water | up to: 100 g |

EXAMPLE NO. 24

VAGINAL FOAM

| SUBSTANCE | QUANTITY FOR 1 UNIT |
|---|---|
| Active substance: | |
| Ketoprofen Glucosamine salt | 17 g |
| equivalent to Ketoprofen acid | 10% |

-continued

| SUBSTANCE | QUANTITY FOR 1 UNIT |
|---|---|
| Excipients: | |
| Sodium Lauryl sulfate | 1 g |
| PVP | 2 g |
| Methyl-p-hydroxybenzoate | 0.1 g |
| Propyl-p-hydroxybenzoate | 0.05 g |
| Benzyl alcohol | 0.5 g |
| Purified water | up to: 100 g |

Packed in a pressurized can with an applicator, dosed at a ratio of 45 g of foam with 5 g of isobutane

EXAMPLE NO. 25
SOLUTIONS FOR EAR APPLICATION

| SUBSTANCE | QUANTITY FOR 1 UNIT |
|---|---|
| Active substance: | |
| Ketoprofen Glucosamine salt equivalent to Ketoprofen acid | 17 g 10% |
| Excipients: | |
| Methyl-p-hydroxybenzoate | 0.1 g |
| Propyl-p-hydroxybenzoate | 0.05 g |
| Propylene glycol | up to: 100 g |

EXAMPLE NO. 26
EYEDROP SOLUTIONS

| SUBSTANCE | QUANTITY FOR 1 UNIT |
|---|---|
| Active substance: | |
| Ketoprofen Glucosamine salt equivalent to Ketoprofen acid | 1.7 g 1% |
| Excipients: | |
| Sodium chloride | 0.9 g |
| Benzalconium chloride | 0.1 g |
| Sterile Purified water | up to: 100 ml |

EXAMPLE NO. 27
CREAM

| SUBSTANCE | QUANTITY FOR 1 UNIT |
|---|---|
| Active substance: | |
| Ketoprofen Glucosamine salt equivalent to Ketoprofen acid | 17 g 10% |
| Excipients: | |
| Nesatol | 8 g |
| Xalifin 15 | 15 g |
| Propylene glycol | 3 g |
| Methyl-p-hydroxybenzoate | 0.1 g |
| Propyl-p-hydroxybenzoate | 0.05 g |
| Purified water | up to: 100 g |

EXAMPLE NO. 28
GEL

| SUBSTANCE | QUANTITY FOR 1 UNIT |
|---|---|
| Active substance: | |
| Ketoprofen Glucosamine salt equivalent to Ketoprofen acid | 17 g 10% |
| Excipients: | |
| Natrosol 250 HH | 2 g |
| Propylene glycol | 10 g |
| Methyl-p-hydroxybenzoate | 0.1 g |
| Propyl-p-hydroxybenzoate | 0.05 g |
| Purified water | up to: 100 g |

EXAMPLE NO. 29
OINTMENT

| SUBSTANCE | QUANTITY FOR 1 UNIT |
|---|---|
| Active substance: | |
| Ketoprofen Glucosamine salt equivalent to Ketoprofen acid | 17 g 10% |
| Excipients: | |
| Amerchol CAB | 8 g |
| Methyl-p-hydroxybenzoate | 0.1 g |
| Propyl-p-hydroxybenzoate | 0.05 g |
| Vaseline | up to: 100 g |

EXAMPLE NO. 30
LOTION

| SUBSTANCE | QUANTITY FOR 1 UNIT |
|---|---|
| Active substance: | |
| Ketoprofen Glucosamine salt equivalent to Ketoprofen acid | 17 g 10% |
| Excipients: | |
| Ethyl alcohol 95° | 10 g |
| Glycerin | 10 g |
| Methyl-p-hydroxybenzoate | 0.1 g |
| Propyl-p-hydroxybenzoate | 0.05 g |
| Purified water | up to: 100 ml |

EXAMPLE NO. 31
SOLUTION

| SUBSTANCE | QUANTITY FOR 1 UNIT |
|---|---|
| Active substance: | |
| Ketoprofen Glucosamine salt equivalent to Ketoprofen acid | 17 g 10% |

-continued

| SUBSTANCE | QUANTITY FOR 1 UNIT |
|---|---|
| Excipients: | |
| Methyl-p-hydroxybenzoate | 0.1 g |
| Propyl-p-hydroxybenzoate | 0.05 g |
| Purified water | up to: 100 ml |

EXAMPLE NO. 32
TOPICAL FOAM WITH PROPELLENTS

| SUBSTANCE | QUANTITY FOR 1 UNIT |
|---|---|
| Active substance: | |
| Ketoprofen Glucosamine salt | 17 g |
| equivalent to Ketoprofen acid | 10% |
| Excipients: | |
| Tween 20 | 3 g |
| PVP k 30 | 3 g |
| Methyl-p-hydroxybenzoate | 0.1 g |
| Propyl-p-hydroxybenzoate | 0.05 g |
| Benzyl alcohol | 0.5 g |
| Lavender perfume | 0.2 g |
| Purified water | up to: 100 g |

Packed in a pressurized can with an applicator, dosed at a ratio of 45 g of foam with 5 g of isobutane

EXAMPLE NO. 33
FOAM WITHOUT PROPELLENTS

| SUBSTANCE | QUANTITY FOR 1 UNIT |
|---|---|
| Active substance: | |
| Ketoprofen Glucosamine salt | 17 g |
| equivalent to Ketoprofen acid | 10% |
| Excipients: | |
| Sodium Lauryl sulfate | 1 g |
| PVP | 2 g |
| Methyl-p-hydroxybenzoate | 0.1 g |
| Propyl-p-hydroxybenzoate | 0 05 g |
| Benzyl alcohol | 0.5 g |
| Purified water | up to: 100 g |

Packed in a can with an applicator

What is claimed is:

1. A pharmaceutical preparation comprisinq a hydrosoluble ketoprofen salt obtained by means of a reaction between ketoprofen and glucosamine and/or proline and/or hydroxyoroline.

2. A pharmaceutical preparation in accordance with claim 1, wherein the ketoprofen hydrosoluble salt comprises 0.01 to 30% by mass of the pharmaceutical preparation.

3. An anti-inflammatory or antalqic treatment method for a mammal, the method comprising administering to the mammal the pharmaceutical preparation claimed in claim 1.

4. The method claimed in claim 3, wherein the pharmaceutical preparation comprises an injectable presentation, a tablet, a capsule, a granule or granules, or a suspension.

5. An anti-inflammatory or analgesic treatment method for treating a mucous membrane in a mammal, the method comprising administering to the mammal by injection or topical application the pharmaceutical preparation claimed in claim 1.

6. The method claimed in claim 3, wherein the pharmaceutical preparation comprises a solution, an irrigation solution, a mouthwash solution, a suppository, a vaginal bougie, a gel, a cream, or a foam.

7. A hydrosoluble ketoprofen salt contained in the pharmaceutical preparation claimed in claim 1, wherein the hydrosoluble ketoorofen salt is obtained from ketoorofen and an amino acid in 0.8 to 1.2 times an equimolar cuantity.

8. A hydrosoluble ketoprofen salt as claimed in claim 7 obtained in water solution form, wherein synthesis is carried out at neutral pH at a temperature between 5° and 60° C., wherein in the water solution the obtained hydrosoluble ketoprofen salt has a concentration of $\geq 300$ g·l$^{-1}$.

9. A hydrosoluble ketoprofen salt as claimed in claim 7 obtained in solid form, wherein synthesis is carried out in at least one suitable organic solvent which, after reaction, is eliminated at a high temperature and/or reduced pressure.

10. A pharmaceutical preparation comprising: (1) a ketoprofen glucosamine salt, a ketoprofen proline salt, and/or a ketoprofen hydroxyproline salt; and (2) an excipient.

11. A pharmaceutical preparation as claimed in claim 10 comprising the ketoprofen glucosamine salt and the excipient.

12. A pharmaceutical preparation as claimed in claim 10 comprising the ketoprofen proline salt and the excipient.

13. A pharmaceutical preparation as claimed in claim 10 comprising the ketoprofen hydroxyproline salt and the excipient.

14. A pharmaceutical preparation as claimed in claim 10, wherein the pharmaceutical preparation includes no caffeine.

15. A pharmaceutical preparation as claimed in claim 11, wherein the pharmaceutical preparation includes no caffeine.

16. A pharmaceutical preparation as claimed in claim 12, wherein the pharmaceutical preparation includes no caffeine.

17. A pharmaceutical preparation as claimed in claim 13, wherein the pharmaceutical preparation includes no caffeine.

18. A pharmaceutical preparation in accordance with claim 1, wherein the ketoprofen hydrosoluble salt comprises 0.01 to 30% by mass of the pharmaceutical preparation.

19. An anti-inflammatory or analgesic treatment method for an animal, the method comprising administering to the animal a pharmaceutically effective dose of the pharmaceutical preparation claimed in claim 10.

20. An anti-inflammatory or analgesic treatment method for a joint of an animal, the method comprising administering orally, transdermally, or intramuscularly to the animal a pharmaceutically effective dose of the pharmaceutical preparation claimed in claim 10.

21. The method claimed in claim 19, wherein the pharmaceutical preparation comprises an injectable presentation, a tablet, a capsule, a granule or granules, or a suspension.

22. An anti-inflammatory or analgesic treatment method for treating a mucous membrane in an animal, the method comprising administering to the animal by injection or topical application a pharmaceutically effective dose of the pharmaceutical preparation claimed in claim 10.

23. The method claimed in claim 22, wherein the pharmaceutical preparation comprises a solution, an irrigation solution, a mouthwash solution, a suppository, a vaginal bougie, a gel, a cream, or a foam.

24. A method for preparing the pharmaceutical preparation claimed in claim 10, the method comprising mixing:

(a) the ketoprofen glucosamine salt, the ketoprofen proline salt, and/or the ketoprofen hydroxyproline salt; and (b) the excipient;
  wherein the ketoprofen glucosamine salt comprises a ketoprofen glucosamine salt solution and/or a solid ketoprofen glucosamine salt; wherein the ketoprofen glucosamine salt solution is prepared by dissolving glucosamine base and ketoprofen acid in water to yield the ketoprofen glucosamine salt solution; and wherein the solid ketoprofen glucosamine salt is prepared by dissolving the glucosamine base and the ketoprofen acid in a first solvent and eliminating the first solvent to yield the solid ketoprofen glucosamine salt;
  wherein the ketoprofen proline salt comprises a ketoprofen proline salt solution and/or a solid ketoprofen proline salt; wherein the ketoprofen proline salt solution is prepared by dissolving proline base and the ketoprofen acid in water to yield the ketoprofen proline salt solution; and wherein the solid ketoprofen proline salt is prepared by dissolving the proline base and the ketoprofen acid in a second solvent and eliminating the second solvent to yield the solid ketoprofen proline salt; and
  wherein the ketoprofen hydroxyproline salt comprises a ketoprofen hydroxyproline salt solution and/or a solid ketoprofen hydroxyproline salt; wherein the ketoprofen hydroxyproline salt solution is prepared by dissolving hydroxyproline base and the ketoprofen acid in water to yield the ketoprofen hydroxyproline salt solution; and wherein the solid ketoprofen hydroxyproline salt is prepared by dissolving the hydroxyproline base and the ketoprofen acid in a third solvent and eliminating the third solvent to yield the solid ketoprofen hydroxyproline salt.

25. A method for preparing the pharmaceutical preparation claimed in claim 10, wherein the pharmaceutical preparation comprises: (1) the ketoprofen proline salt and/or the ketoprofen hydroxyproline salt; and (2) the excipient; the method comprising mixing:
  (a) the ketoprofen proline salt and/or the ketoprofen hydroxyproline salt; and
  (b) the excipient;
  wherein the ketoprofen proline salt comprises a ketoprofen proline salt solution and/or a solid ketoprofen proline salt; wherein the ketoprofen proline salt solution is prepared by dissolving proline base and the ketoprofen acid in water to yield the ketoprofen proline salt solution; and wherein the solid ketoprofen proline salt is prepared by dissolving the proline base and the ketoprofen acid in a first solvent and eliminating the first solvent to yield the solid ketoprofen proline salt; and
  wherein the ketoprofen hydroxyproline salt comprises a ketoprofen hydroxyproline salt solution and/or a solid ketoprofen hydroxyproline salt; wherein the ketoprofen hydroxyproline salt solution is prepared by dissolving hydroxyproline base and the ketoprofen acid in water to yield the ketoprofen hydroxyproline salt solution; and wherein the solid ketoprofen hydroxyproline salt is prepared by dissolving the hydroxyproline base and the ketoprofen acid in a second solvent and eliminating the second solvent to yield the solid ketoprofen hydroxyproline salt.

26. A method as claimed in claim 24, wherein the step of dissolving the glucosamine base and the ketoprofen acid in the water occurs at a neutral pH at a temperature between 5° and 60° C.; wherein the ketoprofen glucosamine salt has a concentration of $\geq 300$ g·l$^{-1}$ in the ketoprofen glucosamine salt solution;
  wherein the step of dissolving the proline base and the ketoprofen acid in the water occurs at a neutral pH at a temperature between 5° and 60° C.; wherein the ketoprofen proline salt has a concentration of $\geq 300$ g·l$^{-1}$ in the ketoprofen proline salt solution;
  wherein the step of dissolving the hydroxyproline base and the ketoprofen acid in the water occurs at a neutral pH at a temperature between 5° and 60° C.; and wherein the ketoprofen hydroxyproline salt has a concentration of $\geq 300$ g·l$^{-1}$ in the ketoprofen hydroxyproline salt solution.

27. A method as claimed in claim 24, wherein the first solvent comprises a first organic solvent; wherein the second solvent comprises a second organic solvent; wherein the third solvent comprises a third organic solvent;
  wherein eliminating the first solvent comprises eliminating the first solvent at a high temperature and/or reduced pressure;
  wherein eliminating the second solvent comprises eliminating the second solvent at a high temperature and/or reduced pressure; and
  wherein eliminating the third solvent comprises eliminating the third solvent at a high temperature and/or reduced pressure.

28. A method as claimed in claim 26, wherein the first solvent comprises a first organic solvent; wherein the second solvent comprises a second organic solvent; wherein the third solvent comprises a third organic solvent;
  wherein eliminating the first solvent comprises eliminating the first solvent at a high temperature and/or reduced pressure;
  wherein eliminating the second solvent comprises eliminating the second solvent at a high temperature and/or reduced pressure; and
  wherein eliminating the third solvent comprises eliminating the third solvent at a high temperature and/or reduced pressure.

29. A method as claimed in claim 25, wherein the first solvent comprises a first organic solvent; wherein the second solvent comprises a second organic solvent;
  wherein eliminating the first solvent comprises eliminating the first solvent at a high temperature and/or reduced pressure; and
  wherein eliminating the second solvent comprises eliminating the second solvent at a high temperature and/or reduced pressure.

30. A method as claimed in claim 25, wherein the step of dissolving the proline base and the ketoprofen acid in the water occurs at a neutral pH at a temperature between 5° and 60° C.; wherein the ketoprofen proline salt has a concentration of $\geq 300$ g·l$^{-1}$ in the ketoprofen proline salt solution;
  wherein the step of dissolving the hydroxyproline base and the ketoprofen acid in the water occurs at a neutral pH at a temperature between 5° and 60° C.; and wherein the ketoprofen hydroxyproline salt has a concentration of $\geq 300$ g·l$^{-1}$ in the ketoprofen hydroxyproline salt solution.

31. A method as claimed in claim 30, wherein the step of dissolving the proline base and the ketoprofen acid in the water occurs at a neutral pH at a temperature between 5° and 60° C.; wherein the ketoprofen proline salt has a concentration of $\geq 300$ g·l$^{-1}$ in the ketoprofen proline salt solution;
  wherein the step of dissolving the hydroxyproline base and the ketoprofen acid in the water occurs at a neutral pH at a temperature between 5° and 60° C.; and wherein the ketoprofen hydroxyproline salt has a concentration of ≧300 g·l$^{-1}$ in the ketoprofen hydroxyproline salt solution.

32. An anti-inflammatory or analgesic treatment method for a joint of a mammal, the method comprising administering orally, transdermally, or intramuscularly to the mammal the pharmaceutical preparation claimed in claim 1.

33. A pharmaceutical preparation as claimed in claim 11 for treating a mammal, wherein the pharmaceutical preparation comprises an amount of the ketoprofen glucosamine salt, wherein the amount of the ketoprofen glucosamine salt is at least 0.5 mg for each kg of the mammal.

34. A pharmaceutical preparation as claimed in claim 11 for treating a mammal, wherein the pharmaceutical preparation comprises an amount of the ketoprofen glucosamine salt, wherein the amount of the ketoprofen glucosamine salt is at least 1 mg for each kg of the mammal or at least 2 mg for each kg of the mammal.

35. A pharmaceutical preparation as claimed in claim 11, wherein the pharmaceutical preparation comprises an amount of the ketoprofen glucosamine salt, wherein the amount of the ketoprofen glucosamine salt is at least 85 mg.

36. A pharmaceutical preparation as claimed in claim 11, wherein the pharmaceutical preparation comprises an amount of the ketoprofen glucosamine salt, wherein the amount of the ketoprofen glucosamine salt is at least 170 mg, or at least 1.7 g, or at least 3.4 g.

37. A pharmaceutical preparation as claimed in claim 10 for treating a mammal, wherein the pharmaceutical preparation comprises an amount of the ketoprofen glucosamine salt, the ketoprofen proline salt, and/or the ketoprofen hydroxyproline salt, wherein the amount of the ketoprofen glucosamine salt, ketoprofen proline salt, and/or the ketoprofen hydroxyproline salt is at least 0.5 mg for each kg of the mammal.

38. A pharmaceutical preparation as claimed in claim 10 for treating a mammal, wherein the pharmaceutical preparation comprises an amount of the ketoprofen glucosamine salt, the ketoprofen proline salt, and/or the ketoprofen hydroxyproline salt, wherein the amount of the ketoprofen glucosamine salt, ketoprofen proline salt, and/or the ketoprofen hydroxyproline salt is at least 1 mg for each kg of the mammal or at least 2 mg for each kg of the mammal.

39. A pharmaceutical preparation as claimed in claim 10, wherein the pharmaceutical preparation comprises an amount of the ketoprofen glucosamine salt, the ketoprofen proline salt, and/or the ketoprofen hydroxyproline salt, wherein the amount of the ketoprofen glucosamine salt, the ketoprofen proline salt, and/or the ketoprofen hydroxyproline salt is at least 85 mg.

40. A pharmaceutical preparation as claimed in claim 10, wherein the pharmaceutical preparation comprises an amount of the ketoprofen glucosamine salt, the ketoprofen proline salt, and/or the ketoprofen hydroxyproline salt, wherein the amount of the ketoprofen glucosamine salt, the ketoprofen proline salt, and/or the ketoprofen hydroxyproline salt is at least 170 mg, or at least 1.7 g, or at least 3.4 g.

41. A pharmaceutical preparation as claimed in claim 11, wherein the ketoprofen glucosamine salt comprises 0.01 to 30% by mass of the pharmaceutical preparation.

42. An anti-inflammatory or analgesic treatment method for a joint of a mammal, the method comprising administering orally, transdermally, or intramuscularly to the mammal a pharmaceutically effective dose of the pharmaceutical preparation claimed in claim 12.

43. An anti-inflammatory or analgesic treatment method for a joint of a mammal, the method comprising administering orally, transdermally, or intramuscularly to the mammal a pharmaceutically effective dose of the pharmaceutical preparation claimed in claim 13.

* * * * *